United States Patent
Mercer et al.

(10) Patent No.: US 10,002,407 B1
(45) Date of Patent: Jun. 19, 2018

(54) METHOD AND APPARATUS FOR ENHANCING 3D MODEL RESOLUTION

(71) Applicant: Intermap Technologies Inc., Englewood, CO (US)

(72) Inventors: Nathan Zachary Mercer, Englewood, CO (US); Stephen Charles Griffiths, Englewood, CO (US); Michael John Wollersheim, Englewood, CO (US); Trevor Roy Miller, Englewood, CO (US); Qiaoping Zhang, Englewood, CO (US)

(73) Assignee: Intermap Technologies Inc., Englewood, CO (US)

(*) Notice: Subject to any disclaimer, the term of this patent is extended or adjusted under 35 U.S.C. 154(b) by 0 days. days.

(21) Appl. No.: 15/723,154

(22) Filed: Oct. 2, 2017

Related U.S. Application Data

(60) Provisional application No. 62/544,608, filed on Aug. 11, 2017.

(51) Int. Cl.
  *G06T 3/40* (2006.01)
  *G06T 5/50* (2006.01)
  *G06T 5/00* (2006.01)
  *G06T 5/10* (2006.01)
  *A61B 6/00* (2006.01)

(52) U.S. Cl.
  CPC ............. *G06T 3/40* (2013.01); *A61B 6/5258* (2013.01); *G06T 3/4053* (2013.01); *G06T 5/002* (2013.01); *G06T 5/10* (2013.01); *G06T 5/50* (2013.01); *G06T 2207/20032* (2013.01); *G06T 2207/20182* (2013.01); *G06T 2207/20216* (2013.01); *G06T 2207/20224* (2013.01)

(58) Field of Classification Search
  CPC .......... G06T 3/40; G06T 5/002; G06T 5/003; G06T 5/004; G06T 5/10; G06T 5/50; G06T 2207/20024; G06T 3/4053; G06T 7/73; G06T 2207/20032; G06T 2207/20182; G06T 2207/20216; G06T 2207/20224; A61B 6/5258; A61B 5/0064; G06K 9/46
  See application file for complete search history.

(56) References Cited

U.S. PATENT DOCUMENTS

| | | | | |
|---|---|---|---|---|
| 5,109,430 A | * | 4/1992 | Nishihara | G03F 7/70625 348/87 |
| 5,187,754 A | * | 2/1993 | Currin | G06K 9/0063 375/E7.086 |
| 6,937,775 B2 | * | 8/2005 | Gindele | G06K 9/40 358/3.26 |
| 6,973,218 B2 | * | 12/2005 | Alderson | G06T 5/20 348/E5.081 |

(Continued)

*Primary Examiner* — Manav Seth
(74) *Attorney, Agent, or Firm* — Perkins Coie LLP

(57) ABSTRACT

Systems and methods of enhancing the resolution or restoring details associated with high resolution images into a filtered digital surface model (DSM) for location-based applications and analyses. The disclosed methods include mapping the changing gray scale values (intensity) from the images to changes in elevation in the DSM using a regression over a local neighborhood of pixels. Further, the disclosed methods do not rely on information about the sensor illumination geometry, and are extendable to be able to utilize any types of images. Additionally, the disclosed embodiments are sensor agnostic. That is, the disclosed methods can be applied on any type of images collected by any type of sensor.

20 Claims, 7 Drawing Sheets

(56) References Cited

U.S. PATENT DOCUMENTS

| | | | | |
|---|---|---|---|---|
| 6,978,050 B2 * | 12/2005 | Hunter | G06T 3/4015 | 348/241 |
| 7,043,090 B2 * | 5/2006 | Gindele | G06K 9/40 | 358/1.2 |
| 7,116,838 B2 * | 10/2006 | Gindele | G06K 9/40 | 358/1.2 |
| 7,236,649 B2 * | 6/2007 | Fenney | G06T 9/00 | 375/E7.026 |
| 8,369,579 B2 * | 2/2013 | Frigerio | G06K 9/209 | 382/103 |
| 8,473,264 B2 * | 6/2013 | Barnes | G01V 7/16 | 702/14 |
| 9,830,690 B2 * | 11/2017 | Chiang | H04N 5/20 | |
| 2003/0138152 A1 * | 7/2003 | Fenney | G06T 9/00 | 382/240 |
| 2004/0260471 A1 * | 12/2004 | McDermott | G01V 3/38 | 702/2 |
| 2010/0292973 A1 * | 11/2010 | Barnes | G01V 7/16 | 703/6 |
| 2013/0342736 A1 * | 12/2013 | Numata | G06T 5/002 | 348/241 |
| 2015/0154805 A1 * | 6/2015 | Hsu | G06T 15/04 | 345/420 |
| 2016/0148347 A1 * | 5/2016 | Guido | G06T 3/40 | 382/299 |
| 2017/0358067 A1 * | 12/2017 | Jung | G06T 5/50 | |

\* cited by examiner

| 123 | 124 | 123 | 125 | 129 |
|-----|-----|-----|-----|-----|
| 123 | 123 | 122 | 125 | 126 |
| 120 | 122 | 123 | 124 | 127 |
| 119 | 120 | 121 | 120 | 122 |
| 118 | 119 | 120 | 120 | 120 |

*FIG. 2A*

| 18 | 18 | 15 | 20 | 22 |
|----|----|----|----|----|
| 20 | 20 | 17 | 18 | 21 |
| 18 | 17 | 18 | 21 | 20 |
| 15 | 13 | 14 | 16 | 16 |
| 11 | 13 | 14 | 13 | 15 |

*FIG. 2B*

METHOD AND APPARATUS FOR ENHANCING 3D MODEL RESOLUTION

CROSS-REFERENCE TO RELATED APPLICATIONS

This application claims the benefit of U.S. Provisional Patent Application Ser. No. 62/544,608, filed on Aug. 11, 2017, and entitled "METHOD AND APPARATUS FOR ENHANCING 3D MODEL RESOLUTION," the disclosure of which is hereby incorporated by reference in its entirety.

TECHNICAL FIELD

This disclosure is related to modeling geospatial data. More particularly, the embodiments disclosed herein are directed at enhancing the resolution of geospatial data for location-based applications and analyses.

BACKGROUND

Radar-derived raster digital surface models (DSMs) provide a critical component for many modern applications, including flood risk analysis, telecommunications, pipeline routing, military, agriculture, and others. Interferometric Synthetic Aperture Radar (IFSAR) technologies have historically been able to produce DSMs with resolutions that range from 30 m up to 5 m depending on the sensor design and the operational parameters.

Noise gets introduced to the DSM when the DSM is processed at the same resolution as the image(s) from which the DSM is derived. The noise reduces the vertical accuracy of the data and can obscure spatial features that would otherwise be detectable. To address this issue, filtering is normally applied. However, filtering typically reduces the noise level at the expense of DSM resolution. This results in the DSM being generated at a lower resolution than the original images, e.g., as much as 4-8 times lower resolution than the image. Accordingly, there is a need for methods to recover the DSM resolution that gets lost due to filtering of the noise.

BRIEF DESCRIPTION OF THE DRAWINGS

FIG. 2A shows a sample neighborhood kernel associated with surface feature elevations.

FIG. 2B shows image gray values corresponding to the surface feature elevations of FIG. 2A.

DETAILED DESCRIPTION

Figure 1A:
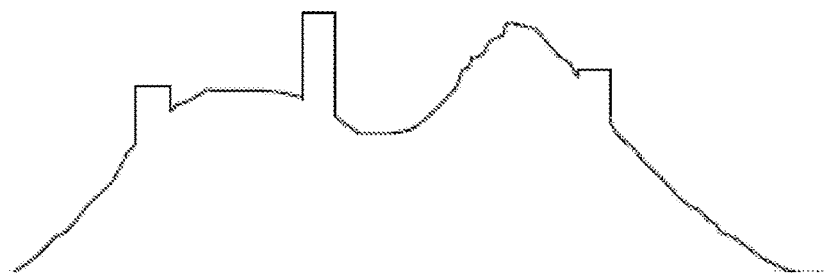
FIG. 1A shows a diagrammatic example of a DSM surface.

This disclosure is directed at systems and methods of enhancing or restoring details associated with high resolution images into a filtered DSM. The disclosed methods include mapping the changing gray scale values (intensity) from the images to changes in elevation in the DSM using a regression over a local neighborhood of pixels. Further, the disclosed methods do not rely on information about the radar illumination geometry, and are extendable to be able to utilize any types of images (e.g. optical images). Although, the present discussions are couched using examples of IFSAR DSMs and images, the technique is generalizable to include DSMs and images from any source and any resolution scale. Additionally, since the present methods do not attempt to reconstruct a surface normal vector, the performance of the methods in enhancing resolution of the DSMs are similar regardless of terrain slope.

The disclosed method takes a model (e.g., a DSM) as input and improves the spatial content and resolution using an image that includes more features than those included in the model. The method is applicable to DEMs and images generated from any sensor technology, including but not limited to IFSAR. Further, the disclosed methods are not dependent on the resolution scale of the input model. The methods can be applied to models of any resolution scale, using imagery of any resolution scale, when the imagery includes features that are not evident in the model. Additionally, the disclosed embodiments are sensor agnostic. That is, the disclosed methods can be applied on any type of images collected by any type of sensor. Examples of image types can be a thermal image, a multi-spectral image, a hyper-spectral image, an optical image, a medical image, a radar image, a weather image, a fused image from multiple types of sensors, a color image, a gray scale image, or a LiDAR intensity image, or any image spatially referenced to the DSM associated with the disclosed methods.

In some embodiments, shape-from-shading (SFS) methodologies are used to extract higher resolution information from images and translate such information into improved terrain definition in the elevation data. Conventional SFS methodologies are based on advanced knowledge about radar image phenomenology in order to properly utilize the radar geometry. These methods, however, are affected by common radar imaging phenomena like speckle, foreshortening and layover. Such phenomena can introduce undesirable artifacts or changes in the gray values of images. These methodologies are also very specific to the sensor technology being used. For example, shape-from-shading techniques for radar imaging are very different than they are for optical imaging, and both are dependent on sensor characteristics and imaging geometry. Furthermore, shape-from-shading techniques exploit variations in the image gray values to reconstruct a normal vector to the DSM surface at each image location, which although useful for accentuating changes in sloped areas, do not offer significant enhancement in flat terrain.

In some embodiments, the disclosed methods are applied to images contemporaneously when the DSM is generated. In some embodiments, errors between the geo-registration quality of the DSM and the images are avoided or minimized. Avoiding or minimizing the errors results in avoiding undesirable spatial features to be added at incorrect locations in the DSM.

IFSAR systems use two antennae separated by an interferometric baseline (B) to image the earth's surface by transmitting radar pulses toward the terrain. The reflected energy is recorded by both antennae, simultaneously providing the system with two SAR images that include amplitude and phase of the same point on the ground, with the two images being separated only by the phase difference created by the space between the two antennae. In addition, as the aircraft passes over the terrain, global positioning system (GPS) data from both aircraft- and ground-based GPS devices as well as navigation data from an inertial measurement unit (IMU) onboard the aircraft can be collected. This navigation data is processed to provide the precise position of the aircraft.

The phase difference between the antennae for each image point, along with range, baseline, GPS, and navigation data, is used to infer the precise topographic height of the terrain being imaged. This enables the creation of an interferogram (depicting the phase difference) from which the DSMs can be derived. Through additional processing, the disclosed DTM is generated.

The DSM is a topographic model of the earth's surface that can be manipulated using a computer. Surface elevation models play a critical role in applications such as biomass studies, flood analysis, geologic and topographic mapping, environmental hazard assessment, oil and gas, telecommunications, and many other applications. The DSM includes elevation measurements that are laid out on a grid. These measurements are derived from the return signals received by two radar antennae mounted on an aircraft. The signals bounce back from first surface they strike, making the DSM a representation of any object large enough to be resolved, including buildings and roads, as well as vegetation and other natural terrain features.

As technologies advance, the demand for higher resolution DSMs that can meet the specifications of modern applications is rising. In such instances where high accuracy and densely sampled elevation data are desirable objectives, other technologies such as Light Detection and Ranging (LIDAR) and stereo photogrammetry can be employed. However, the costs associated with utilizing these technologies can be prohibitive. The higher cost places a limitation on the extent of data that can practically be acquired. For example, in some situations, the dataset can be limited to a smaller size. When compared against these technologies, in some instances, IFSAR can be a more efficient and economical data collection platform since IFSAR is able to penetrate through cloud, smoke, fog and haze and can collect wider swaths of data by aircraft flying at higher altitudes, yielding greater ground coverage.

Preparing Input

In some embodiments, the disclosed method is based on the raster DSM pixels being coincident with the image pixels. Thus, the first step is that the DSM is resampled so that for every image pixel, there is a corresponding DSM pixel. The resampling can be done using techniques such as bilinear resampling, bicubic resampling, nearest neighbor resampling, natural neighbor resampling, kriging resampling, box average resampling, or box median resampling. In some embodiments, the images for input are in grayscale format with a single intensity value for each pixel. Therefore, if a color optical image is being used, the color image is first converted into a grayscale format.

Isolating Surface Features

Low frequency terrain variations typically have a negative impact on the results because the algorithm maps localized changes in elevation to the image grayscale changes. According to disclosed embodiments, slopes present in the terrain are interpreted as elevation change(s), but are not related to the localized distinguishable grayscale changes in the image. Therefore, these slopes are removed to eliminate this confounding effect and isolate the surface feature elevations.

There are many possible ways to identify the low frequency terrain variations. In some embodiments, low frequency terrain variations are identified by applying a coarse smoothing operation to the DSM. The specific parameters of a smoothing filter (e.g., an averaging filter or a median filter) are selected so that the surface features are removed without over-smoothing the actual terrain. For example, over-smoothing can be prevented by ensuring the filter width is not too large. That is, the filter width is chosen to be large enough to remove the surface features, but no so large that it causes the over smoothing of the terrain. When a smoothing filter is applied to the DSM, the size of the filter is defined typically by the number of raster pixels included in the filter kernel. For example, if a DSM has pixels that are 5 meters wide, and a 5×5 smoothing filter is applied, the filter may have a size of 25 m×25 m. This size of kernel can be effective at smoothing over features that are smaller than 25 m in size. Features larger than this may be smoothed to some degree, but not removed from the DSM. As a side-effect of this process, terrain definition can be reduced to some extent because sharp break and drain lines can be rounded off with a radius proportional to the smoothing filter size. When implementing the smoothing process, the area being operated on is analyzed to select a kernel larger than the largest surface feature that needs to be removed. As an example, if a particular area has buildings that are no larger than 18 m in length and in width, a 4×4 kernel size (20 m by 20 m based on 5 m pixels) may be effective at removing the surface features while preserving as much terrain definition as possible. If an area has buildings that are 47 m in length and in width, a larger filter can be used (10×10 kernel size for example).

Another approach is to use a Fourier domain filter to identify low-order terrain variations from the DSM and remove the high frequency content. Additional low frequency terrain identification algorithms can be used that may be more complex, but produce superior results. In some embodiments, a Digital Terrain Model (DTM) is used.

The DTM is a topographic model of the bare earth that can be manipulated using a computer. Vegetation, buildings, and other cultural features have been digitally removed from the DTM, leaving just the underlying terrain. (A DTM is created by removing vegetation, buildings, and other cultural features from a DSM. This is achieved using the disclosed methods, according to which terrain elevations are derived from measurements of bare ground included in the original radar data as well as by manually reviewing and editing every pixel. One key feature of a DTM is that the DTM infers the terrain characteristics that may be hidden in the DSM.

Figure 1B:
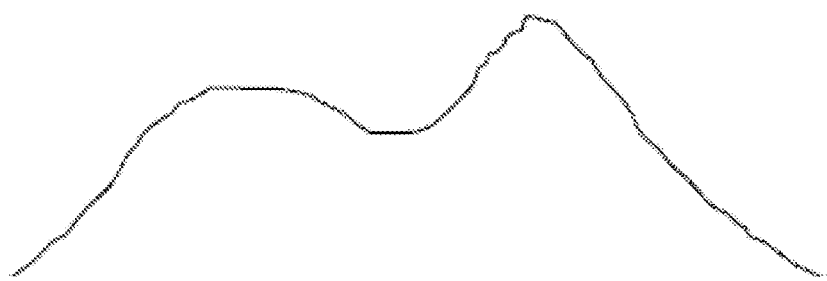
FIG. 1B shows a diagrammatic example of low frequency terrain included in the DSM surface of FIG. 1.
Figure 1C:
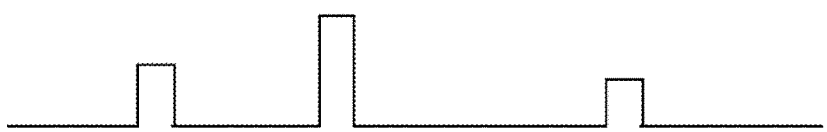
FIG. 1C shows diagrammatic examples of surface features from the DSM surface of FIG. 1A.

Regardless of how the low frequency terrain is obtained, the process of isolating the surface features is based on subtraction of the low frequency terrain from the DSM. The result is a difference surface that is typically flat except for noise and surface features. This process is illustrated in FIGS. 1A-1C and the equation describing the operation is given in Equation (1).

$$\Delta = DSM - T \qquad (1)$$

where:

Δ is the isolated surface features,

DSM denotes the upsampled DSM, and

T is the low frequency terrain.

Adjusting Surface Features

The process operates on the surface features (Δ from Equation (1)) and the grayscale image, iterating on a pixel-by-pixel basis. At each pixel, a correspondence table is constructed that provides a mapping of the difference values (e.g., Δ values) and the image values for all pixels in a neighborhood. The neighborhood size may vary.

FIG. 2A shows a sample neighborhood kernel associated with surface feature elevations included in a difference surface. In FIG. 2A, an example 5×5 kernel is used. The surface elevation values shown in FIG. 2A are multiplied by 100 simply for demonstration purposes, since these values are typically close to zero in a real application. The pixel at the center is an example pixel being operated on.

FIG. 2B shows image gray values corresponding to the surface feature elevations of FIG. 2A. Using the correspondence table of local elevation difference/image gray value pairs, in some embodiments, a linear least squares approach is used to fit a line to the values with the equation:

$$Y = mx + b \qquad (2)$$

where:

Y is the surface feature elevation (Δ), (e.g., shown FIG. 2A)

x is the image gray value, (e.g., shown in FIG. 2B)

m is the slope of the best-fit line, and b is the y-intercept of the best-fit line.

Figure 3:
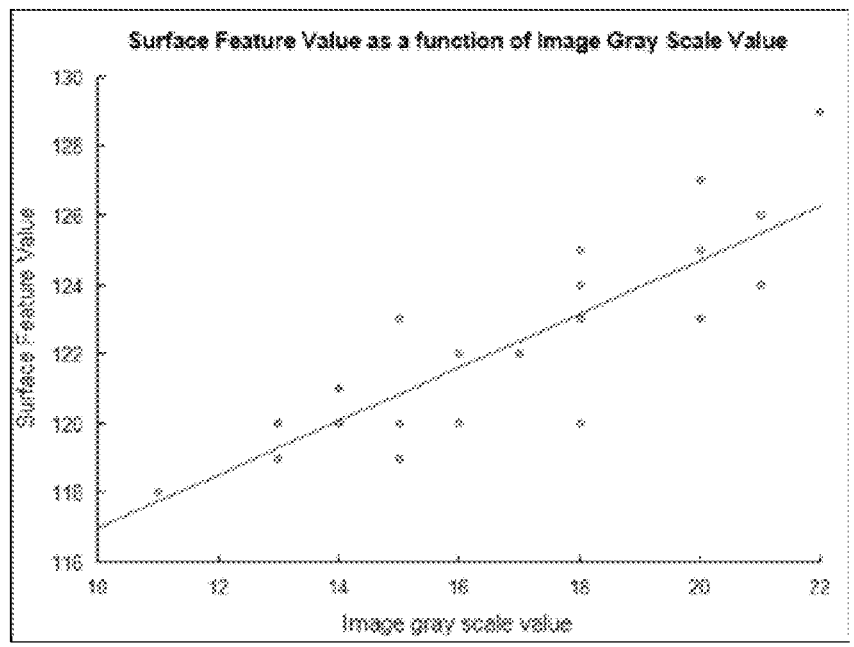
FIG. 3 depicts a line of best fit for the surface feature and gray scale values in FIG. 2A and FIG. 2B respectively.

Using the pixel neighborhood provides a set of points that can be used to determine the slope and intercept values for Equation (2). As an example, the 21×21 pixel neighborhood provides 441 points that can be used to determine the slope and intercept values for Equation (2). Upon determining the slope and intercept, the relationship for mapping gray values to elevation adjustment is established for the specific neighborhood of the target pixel. The adjusted elevation for the target pixel can be computed by applying Equation (2) to the gray value of the target pixel (at the center of the kernel). FIG. 3 depicts a scatter plot of the example values given from FIGS. 2A-2B and shows the best fit line to demonstrate how this works.

After all pixels are adjusted, these surface features are added back to the low frequency terrain surface. This produces the output DSM. According to disclosed embodiments, the output DSM is invariant to changes in one or more pixel values in the original image. A linear model described herein is for discussion purposes only. In some embodiments, the fit/regression model can be a non-linear model, e.g., a second order or a third order model. Further, the neighborhood kernel can be of any size.

Example Results

In some embodiments, the first model and the second model can be generated using a digital surface model (DSM), a weather model, a medical imaging/tomographic model, or a three dimensional (3D) digital model.

Figure 4:
FIG. 4 shows an example input DSM at a native 5 m resolution.
Figure 5:
FIG. 5 shows a radar image at a native resolution of 1.25 m that is associated with the DSM shown in FIG. 4.
Figure 6:
FIG. 6 shows an output DSM corresponding to the radar image shown in FIG. 5.

Results for a sample area are shown in FIGS. 4 through 8. FIG. 4 shows an input DSM at a 5 m resolution. The associated radar image is shown in FIG. 5, with a resolution of 1.25 m. The output DSM (shown in FIG. 6) is generated at 1.25 m resolution using a DTM to obtain the difference surface and a 21×21 kernel size. Comparing FIG. 4 with FIG. 6, it may be seen that details that were not represented in the input DSM in FIG. 4 are included in the output DSM in FIG. 6.

Figure 7:
FIG. 7 shows an optical image corresponding to the geographical area of FIG. 5.
Figure 8:
FIG. 8 shows an output DSM corresponding to the optical image shown in FIG. 7.

To demonstrate the flexibility of the disclosed method, the method is applied to an optical image instead of a radar image. For example, FIG. 7 shows an optical image corresponding to the geographical area of FIG. 4. The optical image in FIG. 7 is at a 1.25 m resolution. FIG. 8 shows the resulting output DSM at 1.25 m resolution when the same parameters are used (DTM difference surface method, with 21×21 kernel size). The results show that the described methods work for both radar and optical images.

In some embodiments, the disclosed methods are applied using an iterative procedure for refining the model for a pre-specified number of iterations. In such embodiments, the second model is produced during the first iteration. The second model becomes the first model in the second iteration. In this iterative procedure, the first iteration can be based on a model that did not fully capture the feature content that was evident in the image. After applying the disclosed methods, the second model is an improvement to the first model and more accurately captures those features. As the iterative procedure continues, the model values move closer to the real values.

In some embodiments, the disclosed methods can be applied progressively, where resolution and feature content are added in stages. For example, the disclosed methods could be used to enhance a 10 m resolution DSM to 1.25 m either directly in one step, or progressively in stages. The stages could be to first enhance from 10 m to 5 m, then from 5 m to 2.5, and then from 2.5 m to 1.25 m, for example. In some applications, a progressive approach produces better results, such as when there is a large gap between the input model resolution and the output model resolution. The second model becomes the first model in the second step. In this progressive procedure, the first step can be based on a model that did not fully capture the feature content that was evident in the image. After applying the disclosed methods, the second model is an improvement to the first model and more accurately captures those features. As the progressive procedure continues, the resolution moves closer to the desired target resolution which is typically the full resolution of the input image (e.g. 1.25 m in this example).

Figure 9:
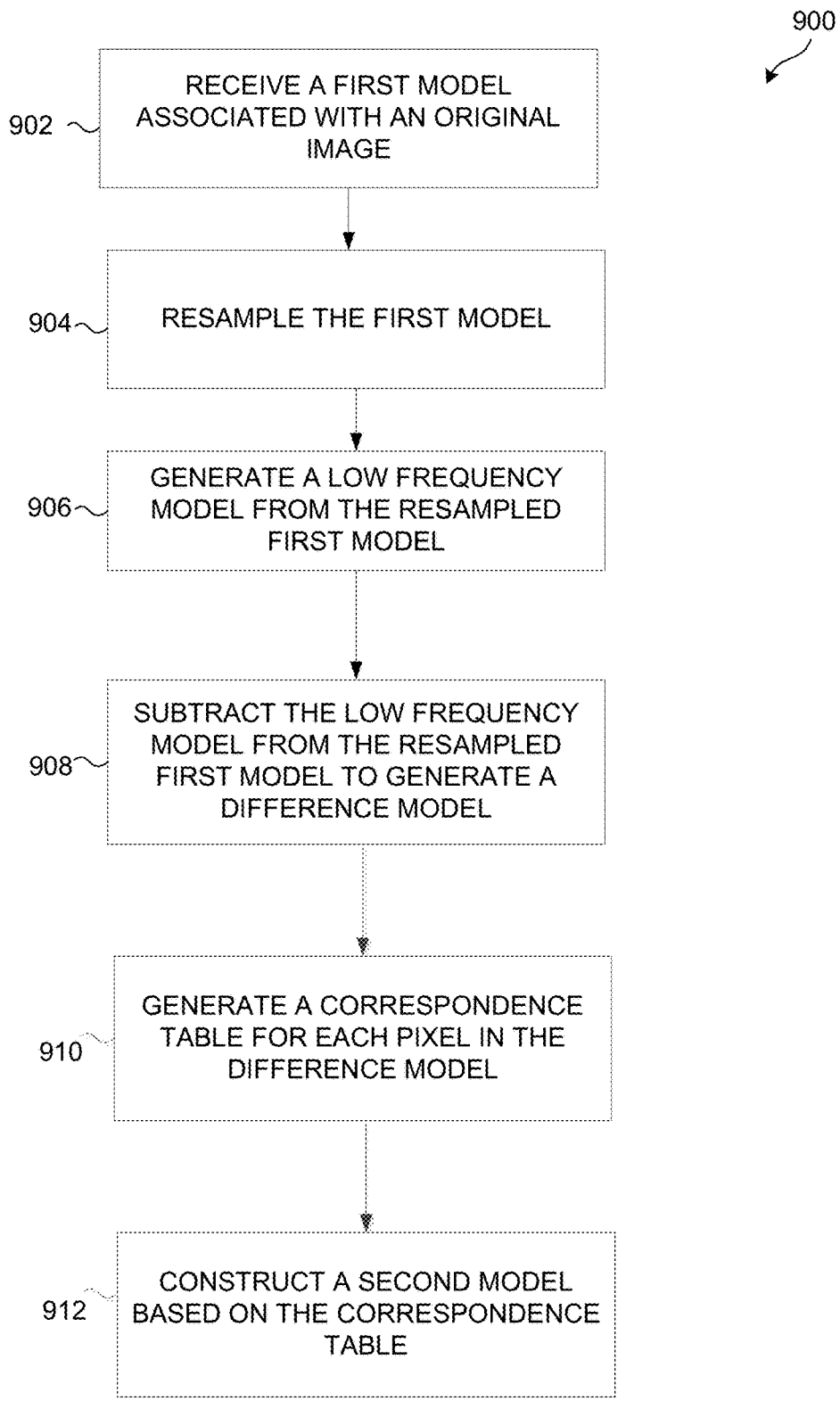
FIG. 9 shows steps of a flowchart associated with enhancing the resolution of geospatial data.

FIG. 9 shows steps of a flowchart associated with a process for enhancing the resolution of geospatial data. At step 902, the step receives a first model spatially referenced or associated with an original image. That is, in some embodiments, the original image used is spatially referenced to the model being enhanced. This implies that the location of each pixel in the image can be translated to a location on the model with a high degree of accuracy. Thus, the disclose methods are able to extract associations between image pixels to locations in the model, so that the image pixels can be used to enhance detail in the model. At step 904, the process resamples the pixels included in the first model. At step 906, the process generates a low frequency model from the resampled first model. At step 908, the process subtracts the low frequency model from the resampled first model for generating a difference surface model. At step 910, the process generates a correspondence table for pixels in the difference surface model by mapping pixels in the difference surface model to a group of pixels in the original image. In some embodiments, the group of pixels in the original image are included in a neighborhood adjacent to a pixel in the difference surface model. In some embodiments, the process extracts grayscale values for pixels At step 912, the process constructs a second model by manipulating grayscale values of the pixels in the original image based on the correspondence table. According to disclosed embodiments, the resolution of the second model is invariant to scale changes in the original image or characteristics of sensors associated with capturing the original image. In some embodiments, the sensor characteristics can be related to the positioning method (for example, orbit model or kinematic positioning solution) of the platform on which the sensors are arranged. In some embodiments, sensor characteristics can be related to the knowledge of the remote sensing geometry (for example, interior and exterior orientation parameters for optical imaging, range-sphere and Doppler cone intersection for radargrammetry, antenna positioning for IFSAR, bore-sighting, and lever arm measurements for many sensor types). In some embodiments, sensor characteristics can be related to the electro-magnetic properties of the imagery produced by each sensor. For example, radar imagery may show variations in the imagery due to differing moisture content in the soil, whereas electro-optical imagery may show such variation. The methods disclosed herein are invariant to sensor characteristics.

This document discloses a new method for enhancing DSM resolution and spatial content by using detailed images to guide the resampling procedure. The method presented can be applied to optical or radar image inputs, and performs consistently regardless of terrain slope. That is, the disclosed methods equally enhance the resolution of equally two identical features, even if one of those features is on highly sloped terrain, while the other is on flat terrain. In other words, the presence of slope(s) of the terrain has/have no effect on the performance of enhancement of the resolution of the features on the terrain. Additionally, the disclosed methods are easier to implement than traditional shape from shading techniques and can be applied to input DSM sources of any resolution scale.

The results (depicted in FIGS. 4-8) of applying the disclosed method demonstrate enhanced resolution in the output DSM with detailed feature content coming from the image that is not present in the input DSM. Resolution is increased at least by a factor of 4 in these cases, which is sufficient, e.g., for enabling applications that demand higher accuracy and more densely posted terrain information. The disclosed methods can also be applied for rapidly updating and improving existing DSMs without re-acquiring the elevation data.

Some of the embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media may include a non-transitory storage media. Generally, program modules may include routines, programs, objects, components, data structures, etc. that perform particular tasks or implement particular abstract data types. Computer- or processor-executable instructions, associated data structures, and program modules represent examples of program code for executing steps of the methods disclosed herein. The particular sequence of such executable instructions or associated data structures represents examples of corresponding acts for implementing the functions described in such steps or processes.

Some of the disclosed embodiments may be implemented as devices or modules using hardware circuits, software, or combinations thereof. For example, a hardware circuit implementation may include discrete analog and/or digital components that are, for example, integrated as part of a printed circuit board. Alternatively, or additionally, the disclosed components or modules may be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application. Similarly, the various components or sub-components within each module may be implemented in software, hardware or firmware. The connectivity between the modules and/or components within the modules may be provided using any one of the connectivity methods and media that is known in the art, including, but not limited to, communications over the Internet, wired, or wireless networks using the appropriate protocols.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems, and computer program products.

The invention claimed is:

1. A computer-implemented method comprising:
 receiving a first model associated with an original image;
 resampling the first model for one or more pixels in the original image;
 generating a low frequency model from the resampled first model;
 subtracting the low frequency model from the resampled first model for generating a difference model;
 generating a correspondence table for pixels in the difference model by mapping each pixel in the difference model to a group of pixels in the original image, wherein the group of pixels are included in a neighborhood adjacent to a pixel in the difference model; and
 upon extracting grayscale values for the one or more pixels in the original image, constructing a second model by manipulating the grayscale values of the one or more pixels in the original image based on the correspondence table, wherein a resolution of the second model is invariant to scale changes in the original image or characteristics of sensors associated with capturing the original image.

2. The method of claim 1, wherein resampling the first model is based at least on: bilinear resampling, bicubic resampling, nearest neighbor resampling, natural neighbor resampling, kriging resampling, box average resampling, or box median resampling.

3. The method of claim 1, wherein resampling the first model includes determining that each pixel in the resampled first model is associated with a corresponding pixel in the original image.

4. The method of claim 1, further comprising:
upon determining that the original image is not in a grayscale format, converting the original image to a grayscale format for extracting the grayscale values for the one or more pixels in the original image.

5. The method of claim 1, wherein the low frequency model is generated using at least one of: a Digital Terrain Model (DTM), a Fourier Domain filter that removes the high frequency content, a spatial smoothing filter.

6. The method of claim 1, wherein the low frequency model is generated using a smoothing filter, wherein the parameters of the smoothing filter (i) prevent over-smoothing features included in the original model and (ii) remove one or more surface features from the original model.

7. The method of claim 1, wherein the low frequency model is generated using a Fourier domain filter that isolates low-order variations from the first model.

8. The method of claim 1, wherein the neighborhood adjacent to each pixel in the difference model is a kernel of a predetermined size.

9. The method of claim 1, wherein the resolution of the second model is higher than a resolution of the first model.

10. The method of claim 1, wherein the resolution of the second model is invariant of slopes of features included in the original image.

11. The method of claim 10, wherein the second model is constructed contemporaneously to receiving the first model.

12. The method of claim 1, wherein the original image is at least one of: a thermal image, a multi-spectral image, a hyper-spectral image, an optical image, a medical image, a radar image, a weather image, a fused image from multiple types of sensors, a color image, a gray scale image, or a LiDAR intensity image.

13. The method of claim 1, wherein the first model and the second model correspond to a digital surface model (DSM), a tomographic model, a weather model, or a three dimensional (3D) digital model.

14. The method of claim 1, wherein manipulating the grayscale values based on the correspondence table includes generating a regression table from the correspondence table.

15. The method of claim 14, wherein the regression model corresponds to a linear model.

16. The method of claim 14, wherein the regression model corresponds a non-linear model.

17. A non-transitory computer-readable storage medium storing instructions configured to cause at least one computing device to perform a method comprising:
receiving a first model associated with an original image;
resampling the first model for one or more pixels in the original image;
generating a low frequency model from the resampled first model;
subtracting the low frequency model from the resampled first model for generating a difference model;
generating a correspondence table for pixels in the difference model by mapping each pixel in the difference model to a group of pixels in the original image, wherein the group of pixels are included in a neighborhood adjacent to a pixel in the difference model; and
upon extracting grayscale values for the one or more pixels in the original image, constructing a second model by manipulating the grayscale values of the one or more pixels in the original image based on the correspondence table, wherein a resolution of the second model is invariant to scale changes in the original image or characteristics of sensors associated with capturing the original image.

18. The computer-readable storage medium of claim 17, wherein the original image is at least one of: a thermal image, a multi-spectral image, a hyper-spectral image, an optical image, a medical image, a radar image, a weather image, a fused image from multiple types of sensors, a color image, a gray scale image, or a LiDAR intensity image.

19. A computer system comprising:
at least one processor and
at least one memory comprising instructions configured to cause the at least one processor to perform a method comprising:
receiving a first model associated with an original image;
resampling the first model for one or more pixels in the original image;
generating a low frequency model from the resampled first model;
subtracting the low frequency model from the resampled first model for generating a difference model;
generating a correspondence table for pixels in the difference model by mapping each pixel in the difference model to a group of pixels in the original image, wherein the group of pixels are included in a neighborhood adjacent to each pixel in the difference model; and
upon extracting grayscale values for the one or more pixels in the original image, constructing a second model by manipulating the grayscale values of the one or more pixels in the original image based on the correspondence table, wherein a resolution of the second model is invariant to scale changes in the original image or characteristics of sensors associated with capturing the original image.

20. The system of claim 19, wherein the low frequency model is generated using at least one of: a Digital Terrain Model (DTM), a Fourier Domain filter that removes the high frequency content, or a spatial smoothing filter.

* * * * *